United States Patent [19]

Ochi et al.

[11] Patent Number: 4,540,063
[45] Date of Patent: Sep. 10, 1985

[54] SOUND WAVE ATTENUATION DEVICE

[75] Inventors: Akira Ochi, Tokyo; Toshihiko Asada, Komae, both of Japan

[73] Assignee: Park Trading Co., Ltd., Tokyo, Japan

[21] Appl. No.: 635,004

[22] Filed: Jul. 27, 1984

[30] Foreign Application Priority Data

Aug. 3, 1983 [JP] Japan ................. 58-141119

[51] Int. Cl.³ ............................................. A61B 7/02
[52] U.S. Cl. ................................... 181/135; 181/132; 128/152
[58] Field of Search ............... 181/129, 130, 132, 134, 181/135; 128/152

[56] References Cited

U.S. PATENT DOCUMENTS 2,487,038 11/1949 Baum .................... 181/135
2,619,960 12/1952 Reynolds ................ 128/152

FOREIGN PATENT DOCUMENTS 453603 12/1949 Italy ..................... 181/135

Primary Examiner—Benjamin R. Fuller
Attorney, Agent, or Firm—Limbach, Limbach & Sutton

[57] ABSTRACT

A sound attenuation device is disclosed which is capable of simultaneously attenuating sound waves of both high and low frequencies bands while leaving other frequencies undisturbed. The device is comprised of an outer shell having inlet and outlet apertures at its opposite ends and containing a pair of sound absorbing plates having a pair of thin sheets of a fabric of substantial air permeability and elasticity disposed therebetween and forming an air chamber between the sheets.

20 Claims, 6 Drawing Figures

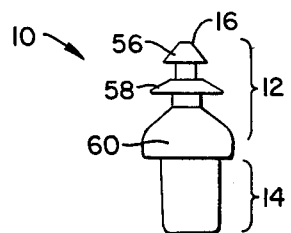
FIG._1.
FIG._3.
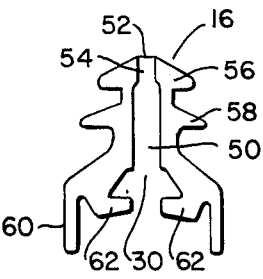
FIG._5.
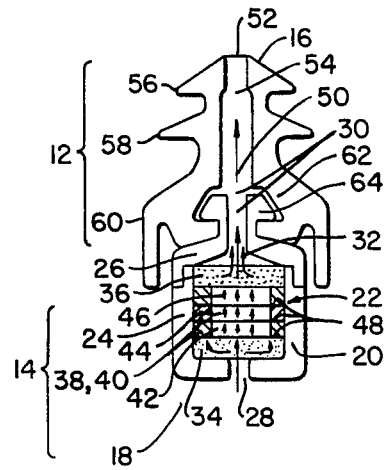
FIG._2.
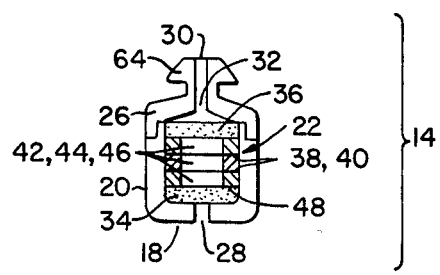
FIG._4.
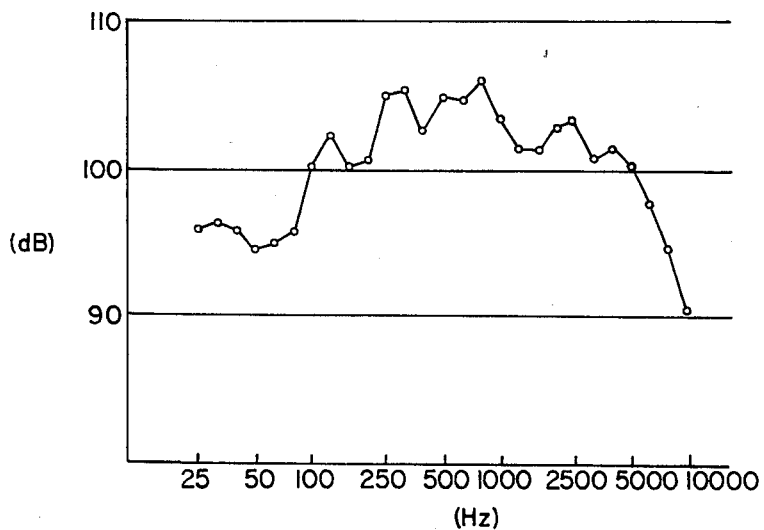
FIG._6.

SOUND WAVE ATTENUATION DEVICE

DESCRIPTION

TECHNICAL FIELD

The present invention relates to an earplug capable of attentuating sound waves of multiple frequency bands.

BACKGROUND OF THE INVENTION

Environmental sounds are typically comprised of a mixture of various sound wave frequencies. Exposure to sound waves of some frequencies under conditions of severe impact can damage the auditory organ and cause hearing problems, including deafness. Injurious noises such as those caused by explosions or bursts are often comprised of a mixture of sound wave frequencies. These disturbing frequencies are in both the high and low frequency bands. Individuals who are frequently exposed to such disturbing and sometimes dangerous frequencies run the risk of incurring such injury. These individuals include demolition workers and operators of heavy, noisy equipment such as firearms to name only a few.

Sound attenutation devices are known which specifically address this problem. These include conventional earmuffs, earplugs and the like which function to reduce the negative effects of exposure to dangerous frequencies by limiting the entry of all sound waves into the auditory organ. These previous devices, however, suffer from the disadvantage that auditory access to environmental sounds of relatively risk free frequencies is also limited. Use of such previous devices, although protective to some extent against the effects of exposure to dangerous frequencies, creates a new danger of shutting out all environmental sounds including those of speech.

Other devices which are typically comprised of a plurality of sound absorbing plates are known which are capable of filtering out noises of certain sound wave frequencies while leaving others undisturbed. These prior art devices, however selective, cannot simultaneously attenuate sound waves of both high and low frequencies. Rather, they are selective of a limited frequency band. The disadvantage of these devices are obvious inasmuch as many injurious noises are comprised of multiple frequencies.

It is therefore an object of the present invention to provide a device heretofore unkown which is capable of attentuating sound waves of both high and low frequencies bands.

SUMMARY OF THE INVENTION

A sound wave attentuation device is disclosed comprising a outer shell having inlet and outlet apertures at opposite ends and containing a sound wave attentuation unit disposed between the apertures such that environmental sound waves enter the device through the inlet aperture, penetrate the sound wave attentuation unit wherein sound waves are attentuated, and exit the device through the outlet aperture. The sound wave attentuation unit is comprised of a first and a second plate of a sound absorbing material positioned near the inlet and outlet apertures respectively and a pair of thin sheets of a fabric of substantially uniform air permeability and elasticity disposed therebetween and forming an air chamber between the sheets.

An improved earplug is further disclosed which includes the sound wave attentuation device of this invention.

The invention is described below in greater detail with reference to the accompanying drawings.

BRIEF DESCRIPTION OF THE DRAWINGS

FIG. 1 is a side view of an embodiment of the invention wherein the proximal member of the earplug is detachably attached to the distal member of the earplug containing the sound wave attentuation unit.

FIG. 2 is a cross sectional view of FIG. 1 illustrating the sound wave attentuation process.

FIG. 3 is a bottom view of FIG. 1.

FIG. 4 is a cross sectional view of the distal member of FIG. 1

FIG. 5 is a cross sectional view of the proximal member of FIG. 1.

FIG. 6 is a graph illustrating the correlation between noise level and sound wave frequency on clay shooting.

BEST MODE FOR CARRYING OUT THE INVENTION

In the drawings, the intact earplug of the present invention is shown generally as reference numeral 10. As shown in FIGS. 1 and 2, the earplug is generally comprised of a proximal member 12 and a distal member 14. In operation, proximal end 16 is inserted into the external auditory meatus of the ear (not shown) and distal end 18 is exposed to the external environment.

Referring to FIGS. 2 and 4, distal member 14 is comprised of an outer shell 20 in which is housed sound wave attenuation unit 22 of the present invention. To facilitate manufacture, outer shell 20 may be comprised of two complimentary segments 24 and 26. During assembly, sound wave attentuation 22 is placed within segment 24 and segment 26 is joined to the assembly by any suitable means. Outer shell 20 may be comprised of a metal, a synthetic resin or a metal plated synthetic resin. Outer shell 20 also has an inlet aperture 28 and an outlet aperture 30 disposed at opposite ends of distal member 14 defining distal sound wave passageway 32 such that environmental sounds enter the device through inlet aperture 28, penetrate sound wave attenuation unit 22 wherein sound waves are attenuated, exit the distal member and enter proximal member 12 through outlet aperture 30.

Sound wave attenuation unit 22 is comprised of a pair of plates 34 and 36 of a sound absorbing material having continuous, minute voids disposed near apertures 28 and 30, respectively, and substantially perpendicular to the direction of distal sound wave passageway 34. A pair of thin sheets 38 and 40 of a fabric of substantially uniform air permeability and elasticity such as to vibrate sensitively and minutely even against very small vibrations are positioned between plates 34 and 36 and define chambers 42, 44 and 46 within distal sound wave passageway 32.

In the illustrated embodiment, inlet aperture 28 and outlet aperture 30 are approximately 1 millimeter in diameter and are centrally located on opposite ends of distal member 14 and coaxial with sound absorbing plates 34 and 36.

In the preferred embodiment, sound absorbing plates 34 and 36 are 2.5 millimeters in diameter and are capable of absorbing 80 percent of incoming sound waves at 500 Hz. Such sound absorbing plates may be constructed by sintering fine particles of a metal such as aluminum of less than 1 millimeter in diameter so as to obtain a porosity of approximately 40 percent.

In the preferred embodiment, the pair of sheets 38 and 40 are comprised of a non-woven, substantially damp proof material such as tensile, thin paper-like substance of several microns in thickness. Such fabric may be constructed by applying pressure to short polyester filaments.

The device may also include a plurality of soft flexible annular packings 48 layered about and between sheets 38 and 40. Annular packings 48 are approximately 1 millimeter in thickness and may be comprised of a soft rubber. Annular packings 48 serve to position sheets 38 and 40 spaced apart from one another and between plates 34 and 36.

Proximal member 12 is hollow having an inlet aperture 50 and an outlet aperture 52 at its opposite ends and continuous with proximal sound wave passageway 54. Inlet aperture 50 is substantially adjacent to outlet aperture 30 of distal member 14 such that attenuated sound waves exiting the distal member at outlet aperture 30 enter proximal member 12 through inlet aperture 50, travel through proximal sound wave passageway 54 and exit the device through outlet aperture 52.

The proximal member of the preferred embodiment further includes a means of securing the position of the device and ensuring close contact of the proximal member to the external auditory meatus of the ear (not shown) and a means of limiting direct invasion of environmental sound waves into the ear. As illustrated in the drawings, such may be accomplished by placing umbrella shaped flanges 56, 58 and 60 arranged in parallel about the major axis of proximal member 12. Each flange should have a greater outer circumference than the flange which is proximal to it and should be oriented such that convex surfaces of the flanges face proximal end 16 and concave surfaces face distal end 18. The most distal flange 60 should have an outer circumference of a size to fit snugly into the external auditory meatus of the ear. In the illustrated embodiment, flanges 56, 58 and 60 secure the position of the device and ensure close contact of the proximal member to the external auditory meatus of the ear. Flange 60 also functions to intercept direct invasion of environmental sounds into the auditory organ. In FIG. 1, flange 60 has a slightly larger diameter than distal member 14. Where the user of the device is an adult male, the most proximal flange 52 and the most distal flange 60 should have diameters of approximately 9.5 millimeters and 11.0 millimeters, respectively. Where the user is an adult female, flanges 56 and 60 should have diameters of approximately 8.0 millimeters and 9.0 millimeters respectively.

To ensure a comfortable fit, proximal member 12 and flanges 56, 58 and 60 should be comprised of a soft rubber which is harmless to the human body. The material should not be so soft as to cause a sticky feeling upon prolonged use and should therefore have a friction coefficient sufficiently large to prevent degradation even when inserted for a long period of time. Silicon rubber or polyisoprene rubber are suitable materials.

As shown in the illustrated embodiment of the present invention, proximal member 12 may be detachably attached to distal member 14 which enables a user to easily exchange or replace the distal member and sound wave attentuation unit 22 contained therein. As shown in FIGS. 2, 4 and 5, this may be accomplished by providing complimentarily shaped segments 62 on 64 on the distal end of proximal member 12 and the proximal end of distal member 14 respectively.

FIG. 2 illustrates the sound wave attentuation process of the present invention. Incoming environmental sound waves enter the device though inlet aperture 28 and penetrate sound wave attentuation unit 22 and are there attentuated by passing through a series of continuous, minute voids numerously present in sound absorbing plate 34 which scatters the sound waves. The scattered sound waves merge with one another to a great extent in chamber 42. The resulting sound waves cause sheet 38 to minutely vibrate and are thereby absorbed to some extent and then eliminate and attenuate one another in chamber 44. The vibrations of the remaining sound waves are then further absorbed by sheet 40, eliminate and attenuate one another again in chamber 46, are scattered once more by passing through the continuous, minute voids numerously present in sound absorbing plate 36 and merge thereafter. The resulting, attenuated sounds exit sound wave attentuation unit 22 through outlet aperture 30 and enter proximal sound wave passageway 54 through inlet aperture 50 and finally exit the device and reach the eardrum (not shown) by way of outlet aperture 52.

This process of scattering and merging with intermittent absorption and attentuation of sound waves overcomes the disadvantage of the prior sound wave attentuation devices in that attenuation of sound wave frequencies in both high and low frequencies is simultaneously accomplished. FIG. 6 illustrates the correlation between noise level [dB(C)] and sound wave frequency [Hz] on clay shooting. As illustrated, the instaneous impact of sound created by clay shooting is comprised of sound wave frequencies ranging from low frequency bands through high frequency bands in the neighborhood of 10,000 Hz. Effective use of prior devices would require a user to change conventional sound wave attenuation units to correspond to their respective frequency bands. Tests exploring the effectiveness of the device of the present invention on clay shooting frequencies using an ordinary audiometer demonstrated that an effective attenuation of approximately 35 dB was achieved on the central frequency of 4000 Hz at 110 dB . Thus, even if the device of this invention is used under the most severe conditions, as in the case of clay shooting, the device operates such as to attentuate the disturbing sounds to become audible and thereby allows a user to go about his daily life without danger or anxiety even on noisy construction sites and the like.

Although the foregoing invention has been described in some detail by way of illustration and examples for purposes of clarity of understanding, it will be obvious that certain changes and modifications may be practiced within the scope of the appended claims.

We claim:

1. A sound wave attenuation device having an outer shell with a first end having an inlet aperture and a second end having an outlet aperture and a sound wave attenuation unit contained within the outer shell and between and coaxial with the first and second ends forming a sound wave passageway such that environmental sound waves enter the device through the inlet aperture, penetrate said sound wave attenuation unit wherein sound waves are selectively attenuated and exit the device through the outlet aperture; said sound wave attenuation unit comprising:

(a) a first plate of a sound absorbing material positioned near the inlet aperture and substantially perpendicular to the direction of the sound wave passageway;

(b) second plate of a sound absorbing material positioned near the outlet aperture and substantially perpendicular to the direction of the sound wave passageway; and (c) a pair of sheets of a fabric of substantially uniform air permeability and elasticity disposed between said first and second plates and forming an air chamber between said sheets.

2. A sound wave attenuation device according to claim 1 wherein said inlet and outlet apertures are centrally located on and coaxial with said first plate and said second plate, respectively.

3. A sound wave attenuation device according to claim 1 wherein said first and second sound absorbing plates are comprised of finely divided metallic particles.

4. A sound wave attenuation device according to claim 3 wherein said metallic particles are less than 1 millimeter in diameter.

5. A sound wave attenuation device according to claim 3 wherein the metallic particles have a porosity of approximately 40%.

6. A sound wave attenuation device according to claim 1 wherein said fabric is comprised of sheets of compressed polyester fibers.

7. A sound wave attentuation device according to claim 1 further comprising a means for positioning said sheets spaced apart from one another.

8. A sound wave attenuation device according to claim 1 wherein said means for positing said sheets further comprises a plurality of annular packings of a soft and flexible material disposed between and coaxial with said sheets.

9. A sound wave attenuation device according to claim 8 wherein said annular packings are layered between said sheets.

10. An earplug capable of selective sound wave attenuation having a proximal end and a distal end, said earplug comprising:

(a) a distal member comprising an outer shell having a first end with a first inlet aperture and a second end with a first outlet aperture and a sound wave attenuation unit contained within the outer shell and disposed between and coaxial with the first and second ends forming a distal sound wave passageway such that environmental sound waves enter the device through the first inlet aperture, penetrate said sound wave attenuation unit wherein sound waves are selectively attenuated and exit the distal member through the first outlet aperture; said sound wave attenuation unit comprising:

(i) a first plate of a sound absorbing material positioned near the first inlet aperture and substantially perpendicular to the direction of the distal sound wave passageway;

(ii) a second plate of a sound absorbing material positioned near the first outlet aperture and substantially perpendicular to the direction of the distal sound wave passageway; and (iii) a pair of sheets of a fabric of substantially uniform air permeability and elasticity disposed between said first and second plates forming an air chamber between said sheets; and (b) a hollow proximal member defining a proximal sound wave passageway having:

(i) a third end with a second inlet aperture substantially adjacent to the first outlet aperture of the second end of the distal member; and (ii) a fourth end with a second outlet aperture substantially continuous with the proximal sound wave passageway such that the attenuated sound waves exiting the distal member at the first outlet aperture enter the proximal member through the second inlet aperture at the third end and exit the earplug through the second outlet aperture at the fourth end.

11. An earplug according to claim 10 wherein said first and second sound absorbing plates of the sound wave attenuation unit are comprised of finely divided metallic particles.

12. An earplug according to claim 11 wherein said metallic particles are less than 1 millimeter in diameter.

13. An earplug according to claim 11 wherein the metallic particles have a porosity of approximately 40%.

14. An earplug according to claim 10 wherein said fabric of the sound wave attenuation unit is comprised of sheets of compressed polyester fibers.

15. An earplug according to claim 10 wherein said sound wave attenuation unit further comprises a means for positioning said sheets spaced apart from one another.

16. An earplug according to claim 15 wherein said means for positioning said sheets further comprises a plurality of annular packings of a soft flexible material disposed between and coaxial with said sheets.

17. An earplug according to claim 16 wherein said annular packings of the sound wave attenuation unit are layered between said sheets.

18. An earplug according to claim 10 further comprising a means of securing the operational position of the earplug.

19. An earplug according to claim 10 further comprising a means of ensuring invasion of environmental sound waves into said sound wave attenuation unit.

20. An earplug according to claim 10 wherein the proximal member is detachably attached to the distal member.

* * * * *